United States Patent [19]

Abood et al.

[11] Patent Number: 5,508,466

[45] Date of Patent: Apr. 16, 1996

[54] SYNTHESIS OF N-PROTECTED-α-SUBSTITUTED-GLYCINE RACEMIC ESTERS BY ZINC-MEDIATED ADDITION OF ORGANIC HALIDE TO GLYCINE CATION EQUIVALENT

[75] Inventors: Norman A. Abood, Morton Grove; Roger A. Nosal, Buffalo Grove, both of Ill.

[73] Assignee: G.D. Searle & Co., Chicago, Ill.

[21] Appl. No.: 227,217

[22] Filed: Apr. 13, 1994

[51] Int. Cl.$^6$ .................. C07C 269/04; C07C 271/12
[52] U.S. Cl. .................. 560/254; 560/115; 560/157; 435/280
[58] Field of Search .................. 560/24, 115, 157; 435/280

[56] References Cited

U.S. PATENT DOCUMENTS

| | | | |
|---|---|---|---|
| 3,878,043 | 4/1975 | Matta et al. | 435/280 |
| 3,884,958 | 5/1975 | Holden et al. | 560/29 |
| 3,920,730 | 11/1975 | Gleason et al. | 560/160 |
| 3,994,954 | 11/1976 | Gleason et al. | 560/24 |
| 3,997,584 | 12/1976 | Gleason et al. | 558/240 |
| 4,108,854 | 8/1978 | Gleason et al. | 544/277 |
| 4,439,524 | 3/1984 | Schutt | 435/280 |
| 4,716,113 | 12/1987 | Urban | 435/125 |
| 5,212,185 | 5/1993 | Hanson | 514/331 |
| 5,223,535 | 6/1993 | Hanson et al. | 514/489 |
| 5,227,401 | 7/1993 | Hanson et al. | 514/489 |
| 5,246,969 | 9/1993 | Hanson et al. | 514/616 |
| 5,252,591 | 9/1993 | Hanson et al. | 514/357 |

FOREIGN PATENT DOCUMENTS

| | | |
|---|---|---|
| 186977 | 7/1986 | European Pat. Off. . |
| 94/04536 | 8/1992 | WIPO . |
| 94/04518 | 3/1994 | WIPO . |
| 94/04508 | 3/1994 | WIPO . |

OTHER PUBLICATIONS

Burdick & Jackson (1982) *High Purity Solvent Guide*, 2nd Ed. Burdick & Jackson Laboratories, Inc., Muskegon, MI, pp. 128–137.

Taguchi et al. (1988) *Tetrahed. Lett.*, 29(41), 5291–5294.

Williams et al. (1990) *J. Org. Chem.*, 55, 4657–4663.

Schricker et al. (1992) *Biorg. Med. Chem. Lett.*, 2(5), 387–390 in *Chem Abst*, 119, Abst. #96107.

Abood et al. (1994) *Tetrahed. Lett.*, 35 (22), 3669–3672.

Schwicker et al. (1992) *Bioorg. Med. Chem. Lett.*, 2(5), "γ-Chymotrypsin Catalyzed Enantioselective Hydrolysis of Alkenyl-γ-Amino Acid Esters", pp. 387–390.

W. N. Speckamp et al., *J. Org Chem.*, 58, 3259–3268 (1993).

P. Munster et al., *Synthesis*, 223–225 (1987).

H. H. Mooiweer et al., *Tetrahedron*, 45, 4627–4636 (1989).

O. Leukart et al., *Helv. Chem. Acta.*, 59, 2181–2183 (1976).

*Primary Examiner*—John W. Rollins
*Assistant Examiner*—Jon P. Weber
*Attorney, Agent, or Firm*—J. Timothy Keane

[57] ABSTRACT

A method is described for synthesis of N-Boc-L-propargylglycine, a key intermediate used in the preparation of high-potency, orally-active renin inhibitors. This method involves reaction of an organic halide with a glycine cation equivalent, such as methyl N-Boc-2-acetoxyglycine, in the presence of zinc dust to give Boc-protected amino acid derivatives in high yield. Typically useful organic halides are allylic, benzylic and propargylic halides. Resolution of methyl N-Boc-propargylglycine with α-chymotrypsin provides N-Boc-L-propargylglycine in high yield.

3 Claims, No Drawings

SYNTHESIS OF N-PROTECTED-α-SUBSTITUTED-GLYCINE RACEMIC ESTERS BY ZINC-MEDIATED ADDITION OF ORGANIC HALIDE TO GLYCINE CATION EQUIVALENT

FIELD OF THE INVENTION

Renin-inhibiting compounds are known for control of hypertension. Of particular interest herein are methods useful to synthesize key intermediates for preparation of renin inhibiting agents.

BACKGROUND OF THE INVENTION

Renin is a proteolytic enzyme produced and secreted into the bloodstream by the juxtaglomerular cells of the kidney. In the bloodstream, renin cleaves a peptide bond in the serum protein angiotensinogen to produce a decapeptide known as angiotensin I. A second enzyme known as angiotensin converting enzyme, cleaves angiotensin II. Angiotensin II is a potent pressor agent responsible for vasoconstriction and elevation of cardiovascular pressure. Attempts have been made to control hypertension by blocking the action of renin or by blocking the formation of angiotensin II in the body with inhibitors of angiotensin I converting enzyme.

Many classes of compounds have been described as inhibitors of the action of renin or angiotensinogen. Renin inhibitors of most interest are high potency, orally-active compounds having a low-cost method of synthesis.

Several families of renin inhibitor compounds have been described which possess the medicinally-significant properties of high potency and therapeutically-effective oral bioavailability. These families of peptide mimetic renin inhibitors are characterized by the presence of a propargyl moiety attached to glycyl residue within the backbone of the peptide mimetic structure. Other families of peptide mimetic compounds are characterized by the presence of an allyl moiety attached to a glycyl residue within the peptide mimetic backbone.

Renin inhibitors containing propargyl glycyl or allyl glycyl residues are described in published patent documents. For example, EP Appl. #186,977 published 9 Jul. 1986 describes renin-inhibiting compounds containing an alkynyl moiety, specifically a propargyl glycine moiety, attached to the main chain between the N-terminus and the C-terminus, such as N-[4(S)-[(N)-[bis(1-naphthylmethyl)acetyl]-D,L-propargylglycylamino]-3(S)-hydroxy-6-methylheptanoyl]-L-isoleucinol. U.S. Pat. No. 5,212,185 issued 18 May 1993 describes piperidinyl-terminated alkylamino ethynyl alanine amino diol compounds as renin inhibitors. U.S. Pat. No. 5,223,535 issued 29 Jun. 1993 describes propargyl glycine amino propargyl diol compounds as renin inhibitors. U.S. Pat. No. 5,227,401 issued 13 Jul. 1993 describes alkylamino-alkylamino-terminated ethynyl alanine amino diol compounds as renin inhibitors. U.S. Pat. No. 5,246,969 issued 21 Sep. 1993 describes di-propargyl-containing aryl-alkylsulfonyl-terminated amino diol compounds as renin inhibitors. U.S. Pat. No. 5,252,591 issued 12 Oct. 1993 describes pyridinyl/quinolinyl-terminated alkylamino ethynyl alanine amino diol compounds as renin inhibitors. PCT Application WO 94/04508 published 3 Mar. 1994 describes imidazolyl/benzimadazolyl-terminated alkylamino ethynyl alanine amino diol compounds as renin inhibitors. PCT Application WO 94/04518 published 3 Mar. 1994 describes morpholino-thiomorpholino-terminated alkylamino ethynyl alanine amino diol compounds as renin inhibitors. PCT Application WO 94/04536 published 3 Mar. 1994 describes ethynyl alanine amino diol compounds having a piperazinyl-terminated group or a piperazinyl-alkylamino-terminated group as renin inhibitors.

There are many conventional methods known for making protected amino acids which can be used as intermediates in synthesis of a wide variety of peptides and peptide mimetics [W. N. Speckamp et al, *J. Org. Chem.*, 58, 3259–3268 (1993)]. For example, amidoalkylation of C-nucleophiles with glycine cation equivalents has been used to make protected α-substituted glycine derivatives [P. Munster et al, *Synthesis*, 223–225 (1987)]. Also, certain γ,δ unsaturated N-protected α-amino acid methyl esters have been made by coupling allylsilanes with glycine cation equivalents in the presence of a Lewis acid catalyst, but which method when used to react propynyltrimethylsilane with glycidyl cation equivalent gave an unusable Dieis-Alder adduct [H. H. Mooiweer et al, *Tetrahedron*, 45, 4627–4636 (1989)]. Many of these methods are inappropriate for making N-protected α-substituted amino acids because such processes frequently require the presence of a Lewis acid to which certain amino acid protecting groups are sensitive.

All of the earlier-mentioned propargyl-glycine or ethynyl-alanine-containing renin inhibitors are characterized by multi-step synthetic routes involving expensive or hard-to-make intermediates. In particular, these multi-step synthetic routes require the use of a stereo-specific N-protected α-substituted amino acid key intermediate, namely, Boc-protected L-propargylglycine, which is not readily available at low cost from commercial sources. Some methods are known for making this key intermediate. For example, one earlier method involves alkylation of diethylacetamidomalonate with propargyl bromide followed by multi-step manipulations to obtain chiral N-Boc-L-propargylglycine [O. Leukart et al, *Helv, Chem, Acta.*, 59, 2181–2183 (1976)]. In U.S. Pat. No. 5,212,185 published 18 May 1993, there is described a reaction of L-propargylglycine with di-tert-butyl-dicarbonate in the presence of potassium carbonate to make Boc-protected L-propargylglycine intermediate. Because of these complicated multi-step syntheses and the high cost of this L-propargylglycine intermediate, there has been delay in the commercial development of propargylglycine-containing renin inhibitors.

Thus, there remains need for new synthetic routes for making low cost N-protected α-substituted amino acids which can be used in peptide synthesis, particularly for making medicinal products such as renin inhibitors.

DESCRIPTION OF THE INVENTION

Natural and unnatural amino acid derivatives may be prepared by reacting an N-protected-α-substituted-glycine cation derivative of Formula I:

with an organic halide of Formula II:

to provide an N-protected-α-substituted-glycine racemic ester of Formula III:

wherein P is N-protecting group; wherein $R^1$ is selected from hydrido, alkyl, cycloalkyl, alkoxyalkyl, acyl, aralkyl, aryl and aroyl; wherein $R^2$ is selected from alkyl, cycloalkyl, alkoxyalkyl, aralkyl and aryl; wherein X is selected from chloro, bromo and iodo; wherein $R^3$ is a radical selected from alkyl, cycloalkyl, alkoxyalkyl, alkoxycarbonylalkyl, allyl and benzyl, wherein further any of said cycloalkyl, allyl and benzyl radicals may be substituted with one or more moieties selected from alkyl, alkoxy, cyano and phenyl; and wherein $R^3$ is further selected from propargyl and substituted-propargyl radicals of the formula:

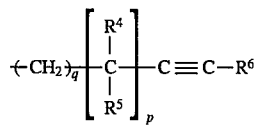

wherein each of $R^4$ and $R^5$ is a radical independently selected from hydrido, alkyl, alkenyl and phenyl; wherein $R^6$ is selected from hydrido, alkyl, benzyl and phenyl; wherein p is a number selected from zero through five, inclusive; wherein q is a number selected from zero through five, inclusive.

The reaction of glycine cation derivative I with organic halide II to provide glycine derivative III proceeds, preferably, in the presence of zinc metal. More preferably the zinc metal is used in a finely-divided form, such as zinc dust. This reaction is usually carried out in a polar aprotic solvent and, preferably, in the absence of a Lewis acid. Examples of suitable polar aprotic solvents are dimethylformamide (DMF), dimethylsulfoxide (DMSO), hexamethylphosphoramide (HMPA) and 1,3-dimethyl-3,4,5,6-tetrahydro-2(1H)-pyrimidinone (DMPU). Typically, the reaction mixture is maintained at a temperature in a range from about 10° C. to about 25° C. during formation of racemic ester derivative III.

Resolution and hydrolysis of racemic ester III with an α-carbon resolution enzyme provides N-protected chiral free acid IV:

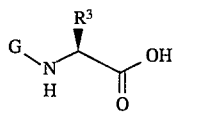

(IV)

wherein P and $R^3$ are as defined above.

The term "N-protecting group" or "N-protected" as used herein refers to those groups intended to protect a nitrogen atom against undesirable reactions during synthetic procedures. Each term includes, but is not limited to, acyl groups such acetyl and t-butylacetyl, pivaloyl, alkoxycarbonyl groups such as methyloxycarbonyl and t-butyloxycarbonyl (Boc), aryloxycarbonyl groups such as benzyloxycarbonyl (Cbz) and fluorenylmethoxycarbonyl (Fmoc), aroyl groups such as benzoyl, and an L- or D-aminoacyl residue which may itself be N-protected similarly.

The hydrolysis reaction is typically carried out at pH in a range from about 6.5 to about 8.5, preferably at a pH of about 8, in the presence of a suitable buffer. Examples of suitable buffers are phosphate and potassium chloride aqueous buffer solutions.

The phrase "α-carbon resolution enzyme" embraces hydrolase enzymes capable of recognizing an α-chiral center of amino acid racemic ester III. Examples of such hydrolase enzymes are α-chymotrypsin, papain, subtilisin and trypsin. A preferred hydrolase enzyme is α-chymotrypsin.

In a preferred embodiment of this method, P is an N-protecting group selected from acyl, pivaloyl, alkoxycarbonyl, aryloxycarbonyl and aroyl; $R^1$ is selected from hydrido, alkyl, cycloalkyl, acyl and benzoyl, wherein said alkyl or alkyl portion of said acyl is a linear or branched moiety of one to about 20 carbon atoms; $R^2$ is a linear or branched alkyl moiety of one to about 20 carbon atoms; X is selected from chloro, bromo and iodo; $R^3$ is a radical selected from alkyl, cycloalkyl, alkoxycarbonylalkyl, allyl, alkyl-substituted-allyl, benzyl, alkoxybenzyl and cyanobenzyl, wherein said alkyl or alkyl portion of said $R^3$ radical is a linear or branched moiety of one to about 20 carbon atoms; and $R^3$ is further selected from propargyl and substituted-propargyl groups of the formula

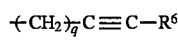

wherein $R^6$ is selected from hydrido and alkyl; and wherein q is a number selected from zero through three, inclusive.

In a more preferred embodiment of this method, P is a protecting group selected from acetyl, t-butylacetyl, benzoyl, methyloxycarbonyl, t-butyloxycarbonyl and benzyloxycarbonyl; $R^1$ is selected from hydrido, alkyl, acyl and benzoyl, wherein said alkyl or alkyl portion of said acyl is selected from methyl, ethyl, n-propyl, isopropyl, n-butyl, isobutyl, sec-butyl, tert-butyl, n-pentyl, iso-pentyl and neopentyl; $R^2$ is selected from methyl, ethyl, n-propyl, isopropyl, n-butyl, isobutyl, sec-butyl, tert-butyl, n-pentyl, isopentyl and neopentyl; X is selected from chloro, bromo and iodo; $R^3$ is selected from alkoxycarbonylalkyl, allyl, alkyl-substituted-allyl, benzyl, alkoxybenzyl and cyanobenzyl, wherein the alkyl portion of any of said $R^3$ radicals is selected from methyl, ethyl and n-propyl; and $R^3$ is further selected from

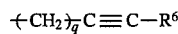

wherein $R^6$ is hydrido or methyl; and wherein q is a number selected from zero through three, inclusive.

In an even more preferred embodiment of this method, P is a protecting group selected from acetyl, t-butylacetyl, benzoyl, methyloxycarbonyl, t-butyloxycarbonyl and benzyloxycarbonyl; $R^1$ is selected from methyl, ethyl, n-propyl, acetyl, propionyl and benzoyl, $R^2$ is selected from methyl, ethyl and n-propyl; X is selected from chloro, bromo and iodo; $R^3$ is selected from ethoxycarbonylmethyl, allyl, methylallyl, benzyl, p-methoxybenzyl and p-cyanobenzyl; and $R^3$ is further selected from

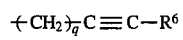

wherein $R^6$ is hydrido or methyl; and wherein q is a number selected from zero through two, inclusive.

The term "hydrido" denotes a single hydrogen atom (H). This hydrido group may be attached, for example, to an oxygen atom to form a hydroxyl group; or, as another example, one hydrido group may be attached to a carbon atom to form a

group; or, as another example, two hydrido groups may be attached to a carbon atom to form a —$CH_2$— group. Where the term "alkyl" is used, either alone or within other terms, the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "alkoxy" embraces linear or branched oxy-containing radicals having alkyl portions of one to about ten carbon atoms, such as methoxy group. The "alkoxy" radical may be further substituted with one or more halo atoms, such as fluoro, chloro or bromo, to provide haloalkoxy groups. The term "acyl" whether used alone, or within a term such as acyloxy, denotes a radical provided by the residue after removal of hydroxyl from an organic acid, an example of such radical being acetyl. "Lower alkanoyl" is an example of a more preferred sub-class of acyl. The term "aryl" embraces aromatic radicals such as phenyl, naphthyl and biphenyl. Preferred aryl groups are those consisting of one, two or three benzene rings. The term "aralkyl" embraces aryl-substituted alkyl radicals such as benzyl, diphenylmethyl, triphenylmethyl, phenylethyl, phenylbutyl and dipenylethyl. The terms "benzyl" and "phenylmethyl" are interchangeable. The term "aroyl" embraces an aryl group attached to a carbonyl radical, such as benzoyl. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkenyl" includes "allyl" and "methylallyl" (or "methallyl") radicals. The term "alkynyl" embraces linear or branched radicals having two to about twenty carbon atoms, preferably two to about ten carbon atoms, and containing at least one carbon-carbon triple bond. The term "alkynyl" embraces "propargyl" and "propargyl-like" moieties which may be optionally substituted with one or more of alkyl, benzyl or phenyl on any substitutable carbon atom. For any of the foregoing defined radicals, preferred radicals are those containing from one to about fifteen carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Generic Scheme

In the following general schemes, there is illustrated a practical application of the general concept of the invention.

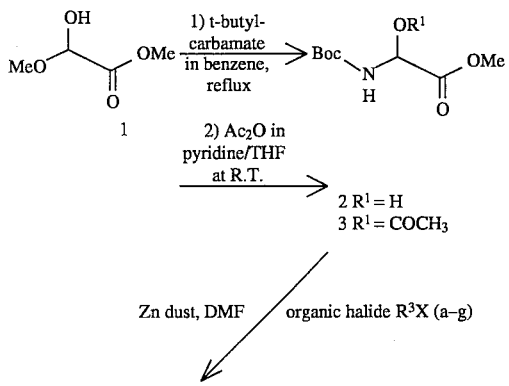

Scheme I:

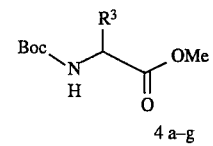

As shown in Scheme I, methyl glyoxalate hemiacetal 1 is condensed with t-butylcarbamate to give the glycine analogue 2. Acylation (acetic anhydride, pyridine, THF) affords the key intermediate methyl 2-acetoxy-2-[((1,1-dimethylethoxy)carbonyl)amino]acetate, 3. Treatment of intermediate 3 with zinc dust in DMF and an organic halide affords amino acid analogues 4 a-g. With regard to synthesis of amino acid analogues 4 a-g, two equivalents of organic halide were added to a 0.5M solution of 3 (2.0 mmol) and zinc dust (4.0 mmol, 325-mesh) in DMF with cooling, at a rate to keep internal temperature between 20°–25° C. Table I, below, shows yields of amino acids 4 a-g after extractive work up and silica gel chromatography. The reaction with organic halide g did not yield the expected p-cyanophenylalanine derivative but instead gave exclusively the substituted phenylglycine derivative, 4 g, in 57% yield, having the structure:

TABLE I

Zinc-Mediated Additions of Organic Halide to Intermediate 3

| Organic Halide | Product (Yield) |
| --- | --- |
| a Br—≡ | 4a (97%) |
| b Br—CO₂CH₂CH₃ | 4b (68%) |
| c Br—CH=CH₂ | 4c (99%) |
| d Br—C(CH₃)=CH₂ | 4d (82%) |
| e Br—CH₂—C₆H₅ | 4e (89%) |
| f Br—CH₂—C₆H₄—OCH₃ | 4f (37%) |
| g Br—CH₂—C₆H₄—CN | 4g (57%) |

It is believed that the selected solvent plays an important role in the formation of amino acid ester 4. For example, using dimethylformamide (DMF), the metallation reaction initiates quickly with intermediate 3 and the addition reaction is usually complete within 1 hour. When the reaction is carried out in tetrahydrofuran (THF), no reaction occurs unless a Lewis acid, e.g., Me₂AlCl (0.5 eq), is present. Even under these conditions, the isolated yields are high and both the Boc group and the ester remain unaffected. It is thus another aspect of this invention that in certain solvents, generally characterized as cyclic-ether type solvents, such as tetrahydrofuran and dioxane, there is permitted the use of a Lewis acid in the synthesis of N-protected α-substituted glycine derivatives. Examples of Lewis acids which may be used in combination with an ether solvent to promote the zinc addition reaction, are dimethylaluminum chloride, methylaluminum dichloride, borontrifluoride etherate complex, ($BF.Et_2O$), titanium (IV) chloride and titanium (IV) dichlorodiisopropoxide, Scheme II:

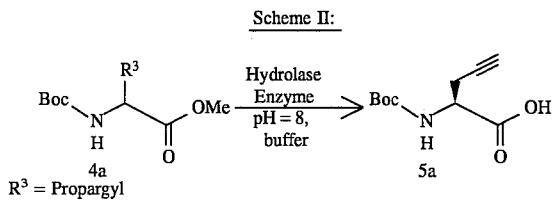

$R^3$ = Propargyl

Resolution of the racemic ester 4a with α-chymotrypsin at 25° C. in 0.1M phosphate buffer (pH 8) afforded N-Boc-L-propargylglycine 5a in 96% yield based on 50% conversion (88% e.e.). One recrystallization from $Et_2O$/petroleum ether gave a 67% yield of 5a enriched to 99% e.e.

Specific Methods

As further exemplification of the generic methods shown in the foregoing General Schemes I and II, there are now shown specific preparations with reactants, amounts, conditions and treatments, for intermediates and amino acid products made by methods of the invention as described in the following Examples 1–5:

EXAMPLE 1

Preparation of methyl 2-[((1,1-dimethylethoxy)carbonyl)amino-2-hydroxyacetate

A solution of methyl glyoxalate hemiacetal (5.66 g, 47.2 mmol) and t-butylcarbamate (5.02 g, 42.9 mmol) in benzene (50 mL) was refluxed for 18 hours. The reaction was concentrated under reduced pressure to approximately one-fifth its volume then stirred rapidly while adding 100 mL of petroleum ether. Stirring continued until a dispersed white solid had formed. The product was filtered, washed with petroleum ether and dried affording 6.64 g (75%) of product (m.p. 96°–97° C.).

Anal. calc'd for $C_8H_{15}NO_5$:C,46.82;H,7.37;N,6.83. Found: C,47.04;H,7.71;N, 6.90.

EXAMPLE 2

Preparation of methyl 2-acetoxy-2-[((1,1-dimethylethoxy)carbonyl)amino]acetate

To a solution of the product of Example 1 (10.0 g, 48.8 mmol), pyridine (7.71 g, 97.6 mmol) and DMAP (300 mg, 2.5 mmol) in THF (50 ML) was added acetic anhydride (5.47 g, 53.6 mmol) slowly at room temperature. After stirring at ambient temperature for 3 hours, the reaction was diluted with EtOAc and washed successively with 1N $NaHSO_4$ and sat'd $NaHCO_3$. The organic phase was dried ($MgSO_4$), filtered and concentrated under reduced pressure affording 11.8 g (98%) of product as a colorless oil.

Anal. calc'd for $C_{10}H_{17}NO_6·1/4H_2O$: C,47.71; H,7.01;N, 5.56. Found: C,47.68;H,6.75;N,5.55.

EXAMPLE 3

Preparation of methyl 2-[((1,1-dimethylethoxy)carbonyl)amino]-4-pentynoate

To an ice cooled suspension of the product of Example 2 (4.00 g, 16.2 mmol) and zinc dust (2.63 g, 40.5 mmol) in DMF (30 mL) under nitrogen was added slowly via syringe propargyl bromide (80% w/w in toluene) (6.02 g, 40.5 mmol). The bromide was added at such a rate as to maintain the internal temperature between 20°–25° C., then stirred at that temperature for an additional 1 hour. The reaction mixture was diluted with 100 mL of EtOAc, washed successively with 0.5N HCl (200 mL), sat'd $NaHCO_3$ (200 mL) and sat'd NaCl and then dried (MgSO4).

After filtration and concentration under reduced pressure, the residue was purified by filtration through a bed of silica gel (30% EtOAc/hexane) to give 3.59 g (97%) of product as a colorless oil after concentration under reduced pressure.

Anal. calc'd for $C_{11}H_{17}NO_4·1/3H_2O$: C,56.64;H,7.63;N, 6.01. Found: C,56.96;H,7.60;H,6.03.

EXAMPLE 4

Preparation of methyl2-[((1,1-dimethylethoxy)carbonyl)amino]-4-pentenoate

To an ice cooled suspension of the product of Example 2 (0.525 mg, 2.12 mmol) and zinc dust (278 mg, 4.25 mmol) in DMF (4 mL) under nitrogen was added slowly via syringe neat allyl bromide (514 mg, 4.25 mmol). The bromide was added at such a rate as to maintain the internal temperature between 20 and 25° C., then stirred at that temperature for an additional 1 hour. Extractive workup and silica gel chromatography as described in Example 3 afforded 486 mg (100%) of product as a colorless oil.

EXAMPLE 5

Preparation of 2(S)-[((1,1-dimethylethoxy)carbonyl)amino]-4-pentenoate

To a suspension of the product of Example 3 (3.53 g, 15.5 mmol) in 60 mL of a 0.1M phosphate buffer (pH 8) was added α-chymotrypsin (25 mg). The reaction mixture was stirred at 25° C. for 22 hours while the pH was kept constant within a range of 7.5–8 by the periodic addition of 1N NaOH. After the unreacted ester was recovered by extracting with EtOAc, the aqueous fraction was acidified (pH 3) with 2N HCl and extracted with EtOAc. During the first extraction of the acidic fraction, the precipitated enzyme made partitioning of the two layers difficult. As a result, the biphasic mixture was filtered through a bed of celite. The layers were then separated and the aqueous phase was extracted again with EtOAc. The organic fractions were combined, dried (MgSO4), filtered and concentrated under reduced pressure affording 1.53 g (92% based on 50% conversion) of product as a viscous oil (88% e.e.). Crystallization of the product from EtO/petroleum ether gave 1.00 g (61%) of product (m.p. 84°–85° C., 99% e.e.). Enantiomeric purity was determined by chiral HPLC analysis using a Crownpak CR(+) column (15 cm×4.6 mm) at 0° C. and isocratic elution with 1% aq. $HClO_4$ at 0.5 mL/min.

The detector was set at 205 nm.

Anal. calc'd for $C_{10}H_{15}NO_4$: C,56.32;H,7.09;N,6.57. Found: C,56.27;H,7.25; N,6.51. $[α]_D^{25}$=+23.5. (MeOH, c=9.1 mg/mL).

The methods of this invention provide economical, high yield synthetic routes for making N-protected amino acid esters using a wide variety of organic halides. In particular, the propargyl-type N-protected amino acid racemic esters may be subjected to hydrolase enzyme resolution to provide, for example, N-Boc-2-propargylglycine, which is an intermediate used in preparation of high-potency, orally-bioavailable renin inhibitor compounds.

Specific examples of renin inhibitor compounds, which may be prepared from this N-Boc-L-propargylglycine intermediate, are shown in Table II, below, along with the published patent documents in which such renin inhibitor compounds appear.

Table II

L-Propargyl-Glycine-Containing Renin Inhibitors

In U.S. Pat. No. 5,212,185 issued 18 May 1993:

Example 1

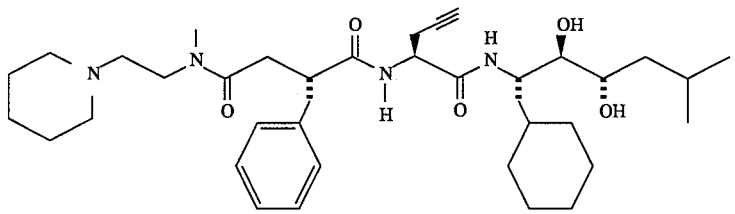

$N^1$-[R*-[[[1S,1R*-(cyclohexylmethyl)-2S*,3R*-dihydroxy-5-methylhexyl]amino]carbonyl]-3-butynyl]-$N^4$-methyl-2S*-(phenylmethyl)-$N^4$-[2-(1-piperidinyl)ethyl]butanediamide Example 2

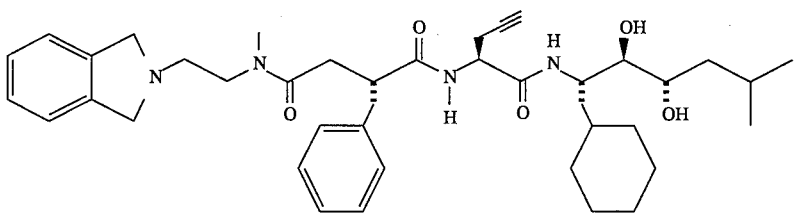

$N^1$-[1R*-[[[1S,1R*-(cyclohexylmethyl)-2S*,3R*-dihydroxy-5-methylhexyl]amino]carbonyl]-3-butynyl]-$N^4$-[2-(1,3-dihydro-2H-isoiondol-2-yl)ethyl]-$N^4$-methyl-2S*-(phenylmethyl)butanediamide Example 3

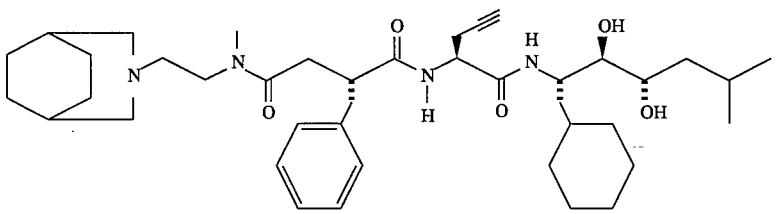

$N^1$-[1R*-[[[1S,1R*-(cyclohexylmethyl)-2S*,3R*-dihydroxy-5-methylhexyl]amino]carbonyl]-3-butynyl]-$N^4$-methyl-2S*-(phenylmethyl)-$N^4$-[2-(N-3-azabicyclo[3.2.2]nonanyl)ethyl]butanediamide In U.S. Pat. No. 5,223,535 issued 29 Jun. 1993:

Example 1

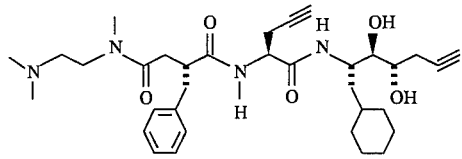

N1-[1R*-[[[1S,1R*-(cyclohexlmethyl)-2S*,3R*-dihydroxy-hexynyl]amino]carbonyl]-3-butynyl]-N4-[2-(dimethylamino)ethyl]-N4-methyl-2S*-(phenylmethyl)butanediamide Example 2

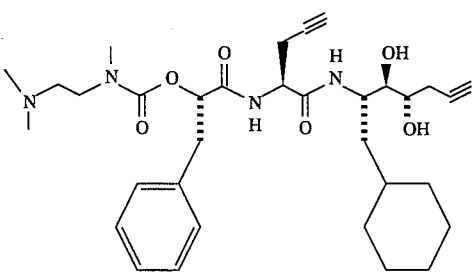

[1R*-[[[1R*-[[[1S,1R*-(cyclohexylmethyl)-2S*,3R*-dihydroxyl-hexynyl]amino]carbonyl]-3-butynyl]amino]carbonyl]-2-phenylethyl)[2-dimethylamino)ethyl]methylcarbamate In U.S. Pat. No. 5,227,401 issued 13 Jul. 1993:

Example 1

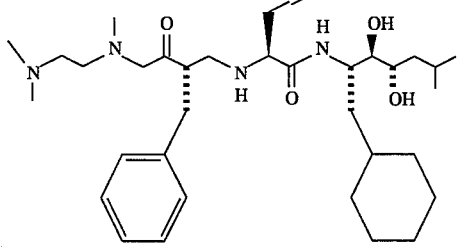

N1-[1R*-[[[1S,1R*-(cyclohexylmethyl)-2S*,3R*-dihydroxy-5-methylhexyl]amino]carbonyl]-3-butynyl]-N4-[2-(dimethylamino)ethyl-N4-methyl-2S*-(phenylmethyl)butanediamide Example 2

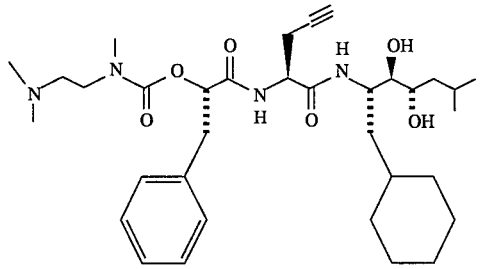

[1R*-[[[1R*-[[[1S,1R*-(cyclohexlmethyl)-2S*,3R*-dihydroxy-5-methylhexyl]amino]carbonyl]-3-butyny]amino]carbonyl]-2-phenylethyl][2-dimethylamino)ethyl]methylcarbamate Example 3

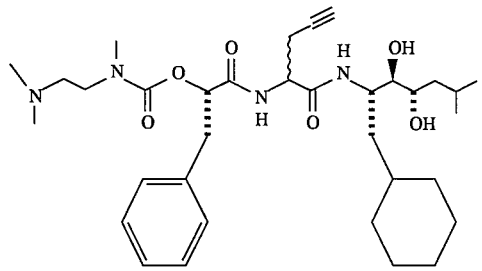

[1R*-[[[1-[[[1S,1R*-(cyclohexylmethyl)-2S*,3R*-dihydroxy-5-methylhexyl]amino]carbonyl]-3-butynyl]amino]carbonyl]-2-phenylethyl][2-(dimethylamino)ethyl]methylcarbamate In U.S. Pat. No. 5,252,591 issued 12 Oct. 1993:

Example 1

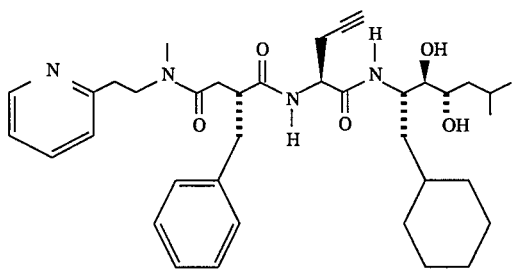

$N^1$-[1R*-[[[1S,1R*-(cyclohexylmethyl)-2S*,3R*-dihydroxy-5-methylhexyl]amino]carbonyl]-3-butynyl]-$N^4$-methyl -2S*-(phenylmethyl)-$N^4$-[2-(2-pyridinyl)ethyl]butanediamide In PCT Application WO 94/04508 Published 3 Mar. 1994:

Example 1

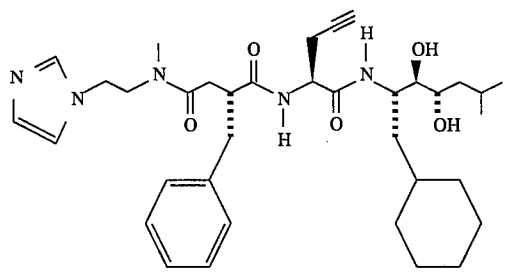

$N^1$-[1R*-[[[1S,1R*-(cyclohexylmethyl)-2S*,3R*-dihydroxy-5-methylhexyl]amino]carbonyl]-3-butynyl]-$N^4$-[2-(1H-imidazol-1-yl)ethyl]-$N^4$-methyl-2S*-(phenylmethyl)butanediamide In PCT Application WO 94/04518 published 3 Mar. 1994:

Example 1

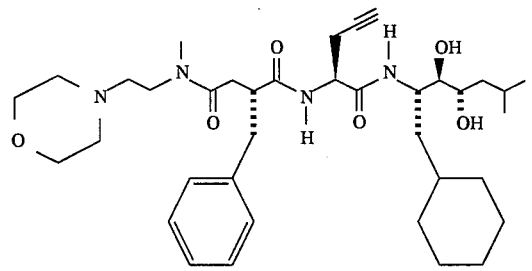

$N^1$-[1R*-[[[1S,1R*-(cyclohexylmethyl)-2S*,3R*-dihydroxy-5-methylhexyl]amino]carbonyl]-3-buynyl]-$N^4$-methyl-$N^4$-[2-(4-morpholinyl)ethyl]-2S*-phenylmethyl)butanediamide In PCT Application No. WO94/04536 published 3 Mar. 1994:

Example 1

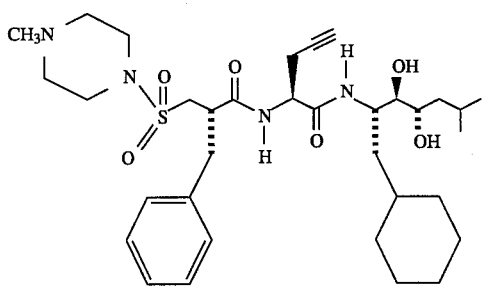

(2S)-2-Benzyl-3-(1-methylpiperazin-4-ylsulfonyl)propionyl-L-propargylglycyl Amide of (2S,3R,4S)-2-amino-1-cyclohexyl-3,4-dihydroxy-6-methylheptane Although this invention has been described with respect to specific embodiments, the details of these embodiments are not to be construded as limitations.

What is claimed is:

1. A method for preparing a naturally occurring or unnaturally occurring amino acid derivative, said method comprising reacting a mixture of elemental zinc and an N-protected-α-substituted-glycine cation derivative of Formula I:

wherein G is the N-protecting group;

wherein $R^1$ is selected from the group consisting of hydrido, alkyl, cycloalkyl, alkoxyalkyl, acyl, aralkyl, aryl and aroyl;

and wherein $R^2$ is selected from the group consisting of alkyl, cycloalkyl, alkoxyalkyl, aralkyl and aryl;

with an organic halide of Formula II:

$$R^3X \qquad \text{(II)}$$

wherein X is selected form the group consisting of chloro, bromo and iodo;

and wherein $R^3$ is a radical selected from the group consisting of alkly, cycloalkyl, alloxyalkyl, alkoxycarbonylalkyl, allyl, benzyl, propargyl and substituted-propargyl radicals of the formula:

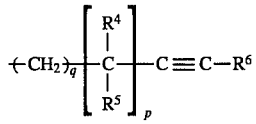

wherein each $R^4$ and $R^5$ is a radical independently selected from the group consisting of hydrido, alkyl, alkenyl and phenyl;

wherein $R^6$ is selected from the group consisting of hydrido, alkyl, benzyl and phenyl;

wherein p is a number selected from zero through five, inclusive; and wherein q is a number selected from zero through five, inclusive;

in a polar solvent to provide an N-protected-α-substituted-glycine racemic ester of Formula III:

wherein G, $R^2$ and $R^3$ are as defined above, and recovering the ester of Formula III.

2. The method according to claim 1 wherein said elemental zinc is zinc metal in a finely divided form.

3. The method according to claim 1 wherein the polar solvent is aprotic and the reaction is performed in the absence of a Lewis acid.

* * * * *